US007419474B2

(12) United States Patent
Lee

(10) Patent No.: US 7,419,474 B2
(45) Date of Patent: Sep. 2, 2008

(54) NON-LINEAR THERAPY SIGNAL SYNTHESIZER

(76) Inventor: Richard Lee, 22 Woodhaven Dr., Laguna Niguel, CA (US) 92677

(*) Notice: Subject to any disclaimer, the term of this patent is extended or adjusted under 35 U.S.C. 154(b) by 332 days.

(21) Appl. No.: 11/324,468

(22) Filed: Jan. 3, 2006

(65) Prior Publication Data

US 2007/0156069 A1 Jul. 5, 2007

(51) Int. Cl.
*A61H 23/02* (2006.01)
*A61N 1/00* (2006.01)

(52) U.S. Cl. ............................ 601/47; 601/48; 607/66; 607/68; 607/73

(58) Field of Classification Search .................... 601/1, 601/46–49, 70–74, 79, 80; 607/66, 68, 69, 607/73, 76

See application file for complete search history.

(56) References Cited

U.S. PATENT DOCUMENTS

| | | | | |
|---|---|---|---|---|
| 5,476,481 | A * | 12/1995 | Schondorf | 607/2 |
| 6,188,929 | B1 | 2/2001 | Giordano | |
| 6,461,316 | B1 | 10/2002 | Lee | |
| 6,684,106 | B2 * | 1/2004 | Herbst | 607/66 |
| 6,690,974 | B2 | 2/2004 | Archer | |
| 6,770,042 | B2 | 8/2004 | Lee | |
| 7,167,752 | B2 * | 1/2007 | Lin-Hendel | 607/46 |
| 2001/0031999 | A1 | 10/2001 | Carter | |
| 2002/0055762 | A1 | 5/2002 | Gliner | |

* cited by examiner

*Primary Examiner*—Danton DeMille

(57) ABSTRACT

A method for producing a non-linearly varying therapeutic signal for therapy wherein a string of randomly or nonlinearly varying data increments the input to a mathematical function such as incrementing the phase angle of a sine function to produce a non linearly varying signal for application as therapy. This method also includes inserting upward chirps and sequencing different therapeutic signals to create a composite signal.

11 Claims, 5 Drawing Sheets

Fig. 2C

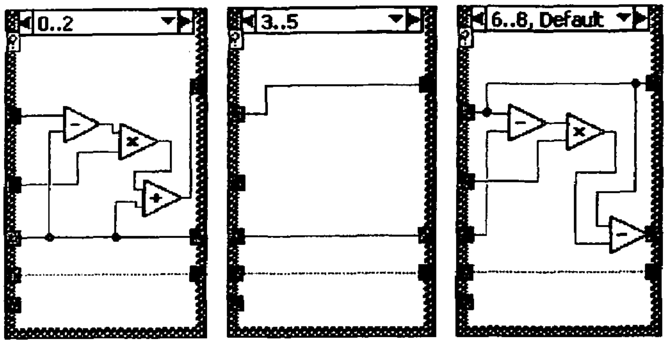

Express VI Configuration Information

Figure 1:
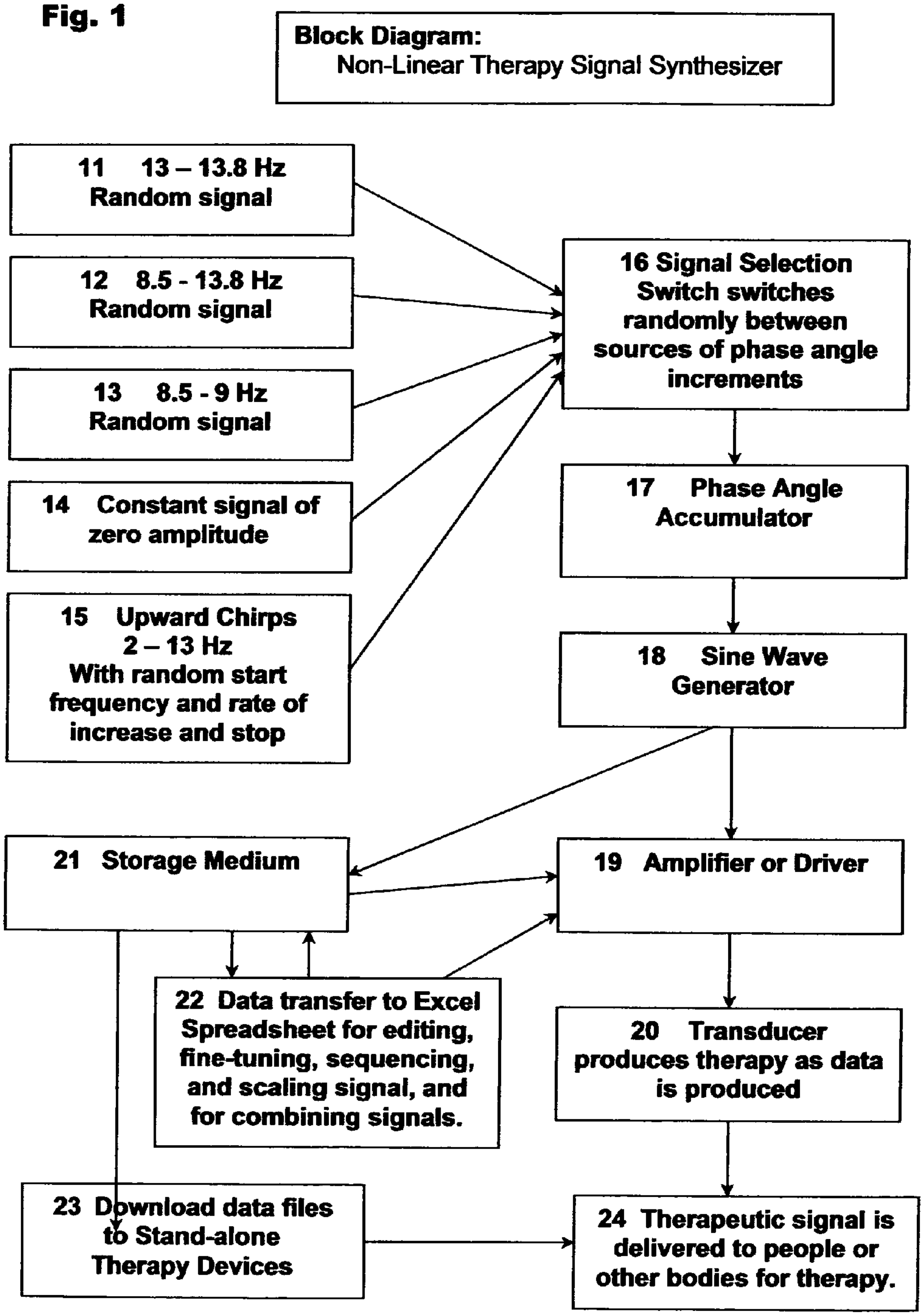
Figure 2A:
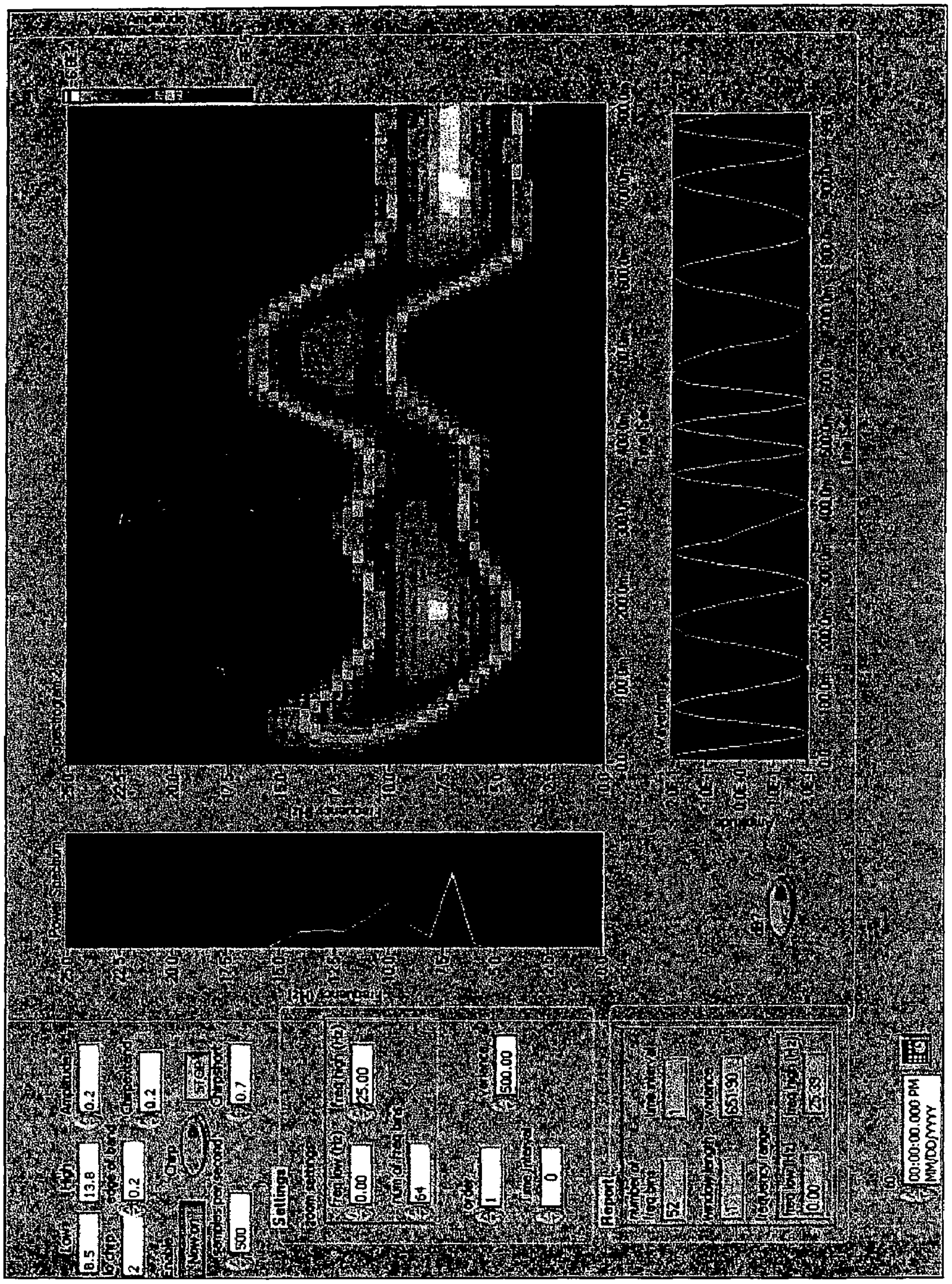
Figure 2B:
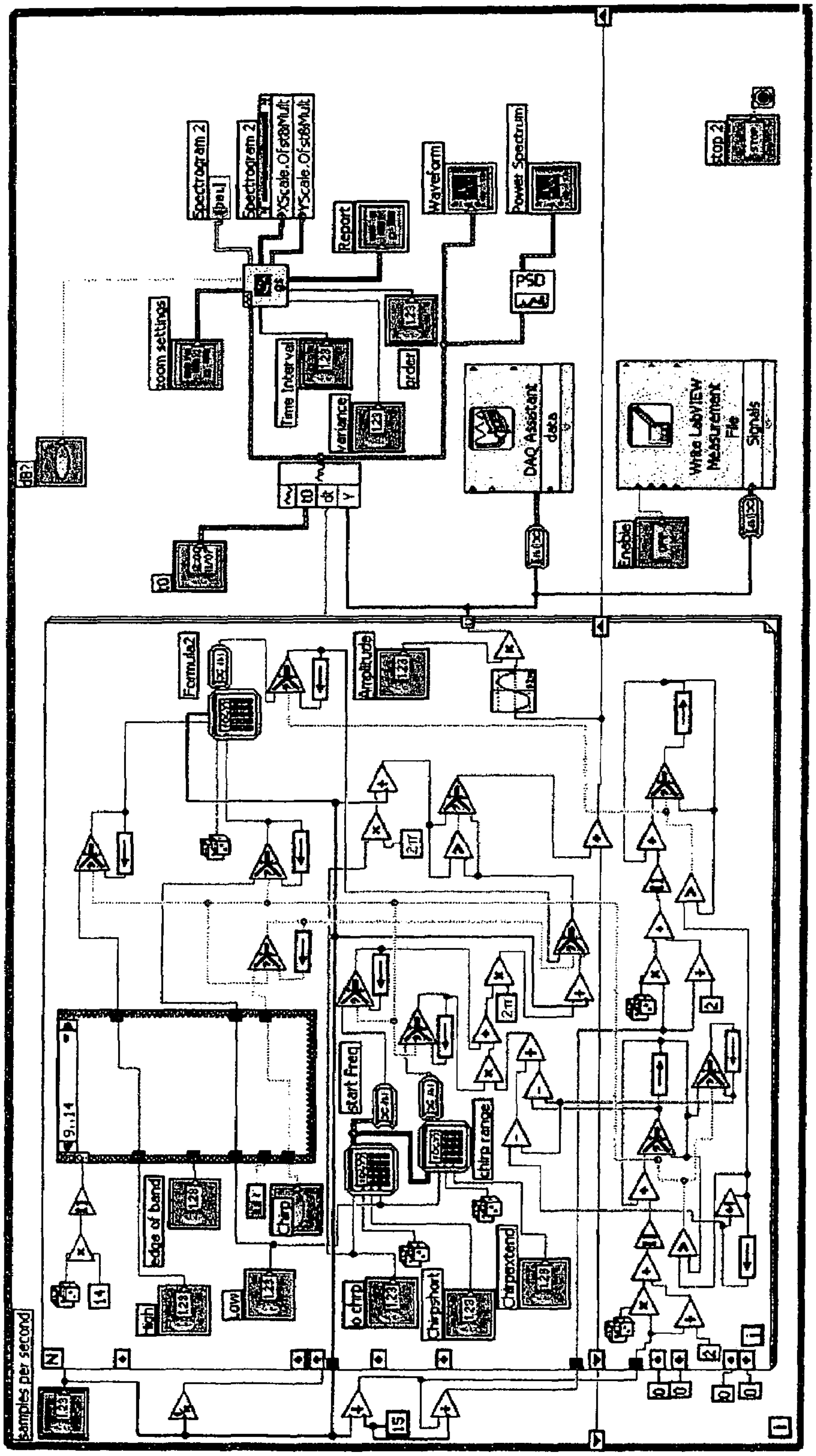

Convert from Dynamic Data
Convert from Dynamic Data

Formula2
Formula
Uses a calculator interface to create mathematical formulas. You can use this Express VI to perform most math functions that a basic scientific calculator can compute.

---

This Express VI is configured as follows:

Formula: (low Freq+rnd*(High Freq-low Freq))*2*pi/Sample frq

DAQ Assistant
DAQ Assistant
Creates, edits, and runs tasks using NI-DAQmx. Refer to the DAQ Quick Start Guide for NI-DAQ 7.0 for information on devices supported by NI-DAQmx.

When you place this Express VI on the block diagram, the DAQ Assistant launches to create a new task. After you create a task, you can double-click the DAQ Assistant Express VI in order to edit that task. For continuous measurement or generation, place a loop around the DAQ Assistant Express VI.

For continuous single-point input or output, the DAQ Assistant Express VI might not provide satisfactory performance. Refer to examples\DAQmx\Analog In\Measure Voltage.llb\Cont Acq&Graph Voltage-Single Point Optimization.vi for techniques to create higher-performance, single-point I/O applications.

Convert to Dynamic Data
Convert to Dynamic Data

Fig. 2D

Write LabVIEW Measurement File
Write LabVIEW Measurement File
Writes data to a LabVIEW measurement data file.

---

This Express VI is configured as follows:

Mode: Save to one file
Filename: alphachirp500.lvm
If a file already exists: Overwrite file
Description:

Convert to Dynamic Data2
Convert to Dynamic Data

Convert from Dynamic Data2
Convert from Dynamic Data

start Freq
Formula
Uses a calculator interface to create mathematical formulas. You can use this Express VI to perform most math functions that a basic scientific calculator can compute.

---

This Express VI is configured as follows:

Formula: lochirp+(low-lochirp)*rnd1*contract

chirp range
Formula
Uses a calculator interface to create mathematical formulas. You can use this Express VI to perform most math functions that a basic scientific calculator can compute.

---

This Express VI is configured as follows:

Formula: low*(1+rnd2*extend)-start

Convert from Dynamic Data3
Convert from Dynamic Data

NON-LINEAR THERAPY SIGNAL SYNTHESIZER

CROSS REFERENCE TO RELATED APPLICATIONS

Therapy devices that deliver signals are very common, though devices that deliver non-linearly varying signals are considerably less common. U.S. Pat. No. 6,461,316, CHAOS THERAPY METHOD AND DEVICE, invented by and registered to me describes a device that produces non-linearly varying signals produced by means of digitally filtering a string of random numbers. U.S. Pat. No. 6,770,042, THERAPEUTIC SIGNAL COMBINATION, also invented by and registered to this inventor describes a device that combines signals with non-linear frequency variation to produce a composite signal. Those patents describe relevant prior art to this patent and are included as reference and as background to the specification of this patent application.

FEDERALLY SPONSORED RESEARCH

Not Applicable

SEQUENCE LISTING OR PROGRAM

LABVIEW® is a proprietary graphical programming environment. A LABVIEW VI or virtual instrument was used in the preferred embodiment of this invention. A printout of the full documentation of the programming of this LABVIEW VI is included as FIG. 1A-D. It is not specifically a program listing since the LABVIEW environment provides for analog virtual instruments, not digital code.

BACKGROUND OF THE INVENTION

Field of Invention

This invention relates to therapeutic devices, specifically to devices capable of delivering a non-linearly varying signal to a living system for therapy.

BACKGROUND OF THE INVENTION

Prior Art

Several patents, including my own prior art listed above, provide related prior art. Here are additional references which, while related to therapeutic signal production, do not disclose, imply, or predict the claims of this patent application.

2002/0055762 describes a device that applies electrical pulses the frequency of which sweeps from less than 4 Hz to above 10 Hz. over a period of more than 6 seconds. This signal can be automatically varied in response to a signal received from a recipient. Similarly, U.S. Pat. No. 6,690,974, in FIG. 18 shows a randomly varying signal which is apparently the result of the device sensing signals from the brain. In both cases, these variations represent biofeedback applications where randomness in a signal is generated by feedback from the recipient.

US 2001/0031999 describes combining a mixture of sine waves to generate an arbitrary wave form. This technique, an application of inverse Fourier transform used here to synthesize a pulse for pacemaker applications, provides a repeating pattern, a repeating pulse wave, differentiating it from this invention. The technique, inverse Fourier synthesis is very different from incrementing a sine function with randomly varying phase angle increments.

U.S. Pat. No. 6,188,929 describes a device that delivers pulses of specified frequency, amplitude, and dwell time. It offers a system by which a memory location is randomly selected, delivering a pulse of random frequency, amplitude and dwell time. This method, selecting random frequency, amplitude, and dwell time to produce pulses, is disclosed in my U.S. Pat. No. 6,461,316, and does not relate to the sine wave synthesis method of the current invention.

While devices embodying my prior patents are safe and effective (FDA 510 k Listed), and approximately 20,000 units have been purchased by doctors and end users, several areas for improvement have been identified.

1. While the energy of the signals falls predominantly within the targeted frequency band, some of the power is delivered in frequencies outside said targeted band, limiting the precision, and thus effectiveness of the therapy device.
2. The nature of the digital filters results in constantly changing frequency with fixed phase angle, limiting the unpredictability and entrainment capability of the signal, and thus its effectiveness.
3. The nature of digital filtration does not allow for abruptly changing from one frequency band or mode of signal production to another within a signal.
4. The signal that results from the digital filtration method involves high variability in amplitude, which means low power density and high transducer stress and excursion when peak voltages are applied to the transducer. It also requires higher power supply voltage to the amplifier reproducing the signals. Lowering peaks after the signal is produced introduces frequencies outside the targeted frequency range, or distortion. This means the amplifier and transducer must be designed with excess capacity that is seldom used, lower power efficiency, and shorter transducer and battery life.
5. The digital filtration method does not include insertion of rising chirps, periods of signal with rising frequency, or sequencing of signals without phase angle discontinuities.
6. The digital filtration method results in a rather large data file that must be generated on the fly or stored, to be played by the therapy device, both in number of data points, and in precision of each data point.

All of the above limits are overcome in the present invention.

BACKGROUND OF THE INVENTION

Objects and Advantages

Creating a therapy signal by incrementing a sine function allows for a signal which fits precisely within a frequency band simply by keeping all phase angle increments within that band. By changing from one phase angle increment to another, the frequency of the signal is instantaneously changed without discontinuities in amplitude or phase angle. Further, while the digital filtration method creates transients when starting, stopping, or shifting from one signal to another, simply changing the phase angle increment stream immediately changes the nature of the signal without transients, allowing for sequencing of signals, inserting rising chirps or any other signal changes on-the-fly. The value of rising chirp insertion is a recent and unexpected discovery made possible by the Non-Linear Therapy Signal Synthesizer. This method also produces a signal of uniform amplitude without voltage transients, which means higher RMS power and reduced transients, allowing for reduced amplifier voltage and transducer displacement for the same power output for greater efficiency, longer battery life, and less wear on moving components.

This method allows for specific duration of frequencies or frequency bands. By maintaining a frequency or signal for a period of time, then shifting to another, a new and unexpected therapeutic effect is realized. My theory as to why this works is as follows: The vibrational nature of the body comes into equilibrium with one signal, and with an abrupt shift, must reorganize to accommodate a second signal. This allows for more rapid and more comfortable softening of vibrational patterns within the body. This is just my theory of why sequencing increases effectiveness and comfort, and should not be used to limit the claims in any way.

Finally, this method allows for very compact implementation on memory-limited portable microprocessor systems. The phase angle increments can be as small as 4 bit, and by selecting randomly between different banks of phase angle increments, small amounts of data can be used repeatedly to create a continuous, unpredictable signal, especially considering that the same phase angle increments, started at each different phase angle, will provide a unique signal.

SUMMARY

In accordance with this invention, a method is described to create therapeutic signals of increased effectiveness over previous methods invented by this inventor, in which a string of phase angle increments is fed into a sine function, producing a signal with highly flexible frequency characteristics. (Phase angle increments within specific ranges will produce a signal with precise frequency limits. Further, by inserting a string of increasing phase angle increments into this sine function at irregular times, short segments of rising frequency can be inserted into this therapeutic signal. Further, by shifting, at random intervals, from phase angle increments within one range to those in another range, the resulting therapeutic signal is more comfortable (less frequently causes pain) and more effective. Finally, this method can be implemented in a portable computerized therapy device to provide small memory requirements because of the need to store only phase angle increments rather than entire signals, and low power requirements because amplitude can be constant, using variable frequency rather than variable amplitude to create an irregular "feel" attractive to the user.

This invention applies to generally continuous signals that are not principally made up of impulses and discontinuities. The current embodiment minimizes discontinuities, though some implementations can introduce discontinuities at a point switching between signals. The term "generally continuous signals" in the claims refers to signals that are not dominated by impulses and discontinuities.

DRAWINGS

FIG. 1 shows the basic block diagram of the Non-Linear Therapy Signal Synthesizer in accordance with the preferred embodiment of my invention.

FIG. 2*a*, 2*b*, 2*c*, and 2*d* show the actual documentation printout from LABVIEW 7.1 including the wiring diagram, front panel, and formulas of the virtual instrument, which will run in the LABVIEW 7.1 environment and produces the signals described above. This method can also be implemented in more digital programming languages.

DETAILED DESCRIPTION

Preferred Embodiment FIGS. 1-2

FIG. 1 shows the block diagram of the preferred embodiment. On the left are five subroutines (11-15) which are sources of different phase angle increments, each based on random number. As an example 13-13-8 Hz (11) 8.5-13.8 Hz (12) and 8.5-9 Hz (3) provide a series of values such that one frequency within the specified range is produced for a random interval of about 0.02 seconds, then another random frequency is produced for another random interval of about 0.02 seconds. This pattern continues indefinitely. When upward chirps (15) are selected the program randomly selects a start frequency and end frequency from within the selected frequency range and a random period of time, then proceeds to produce a series of random phase angle increments of increasing phase angle within the selected range.

A Signal selection switch (16) chooses randomly to receive input from one of the phase angle increment sources (11-15) for a randomly determined period of time, passing that phase angle increment to the phase angle accumulator (17) which adds the increment to the phase angle to form a new phase angle, which it passes on to the sine wave generator (18), which in turn generates the next point in the sine wave. Note that this method allows the sine wave to avoid discontinuities when changing from frequency band to frequency band. The new frequency data simply increments the sine wave with an abrupt change in frequency but only an incremental change in phase angle. This is a key benefit to this invention. This continuous data flow is passed onto the storage medium (21) where a file of the signal is written. The signal (each data point as it is generated) is also passed on to an amplifier (19) which produces a computer adjustable voltage of about 3 volts, which, in turn drives a transducer (20) which produces the actual therapeutic signal as it is produced for monitoring, testing and therapeutic application.

Signal files from the storage medium (21) are then transferred to an Excel spreadsheet (22) where they can be scaled, combined, sequenced, shortened and stored again in storage medium (21). While many of these functions could be achieved with a more complicated phase angle generator program, it is often easier to do these manipulations in a spreadsheet or other digital medium. Finally, the completed signals are transferred to stand alone therapy devices (23) which produce the therapy signal (24).

FIG. 2 A-D shows the documentation (computer code) for the preferred embodiment, an actual signal synthesizer (including 11-18 and 21 from FIG. 1) It is a four page document produced by the LABVIEW program which contains all information required to reproduce the synthesizer. A color copy of FIG. 2 A-D is also included because the colors of many of the lines and boxes indicate the type of data that is being processed and are a part of the documentation.

Operation

The LABVIEW Virtual Instrument of FIG. 2A-D, as documented, will run, producing a random signal with imbedded rising chirps that sequences between frequency bands, and with the option to record the signal digitally by pushing a digital button. Further, with transducer attached, it will produce the described therapeutic signal. It will be clearly evident to any person familiar with the art who examines the Virtual Instrument that a wide variety of frequencies, chirps and other effects can be produced by changing variables and inserting additional subroutines, thus, a presentation of the details of the internal structure of the virtual instrument would be burdensome to the reader of this specification.

The files produced by this LABVIEW Virtual Instrument can be opened directly using EXCEL. The specific program used was EXCEL 2003 for WINDOWS XP. Signals can be manipulated as desired, such as scaling (multiplying by a constant), sequencing (cutting and pasting sequences of different signals to create a composite signal), and combining signals by arithmetic addition, multiplication or other formulas. Arithmetically adding two different signals or the same signal at different phase angles creates a signal of varying amplitude, which is sometimes desirable to enhance the feel of the therapy device. EXCEL can also be used to produce hexadecimal and binary files for loading onto the memory of therapy devices by selecting the appropriate built in EXCEL functions. Again, these manipulations will be obvious to anyone familiar with the state of the art.

For clarity in understanding the operation of the preferred embodiment of this invention, the basic signal generator creating the non-linearly varying therapy signals will be discussed below, along with its limitations. Then enhancements will be discussed that made the invention progressively more workable, and additional enhancements that made it more effective:

The basic workhorse of the invention is a virtual instrument that generates said therapeutic signal through a sine wave function that allows the phase angle of a sine wave to be varied incrementally every iteration of the program. To increment this sine wave function a string of non-linearly varying phase angle increments are calculated, with random variables inserted along the way. Every millisecond, a new phase angle increment is fed into an accumulator that maintains the phase angle and feeds it into the sine wave function producing a signal within the desired frequency range (as in the preferred embodiment, 8.5 to 13.8 Hz).

This method, while providing a randomly varying signal, does not provide a workable solution in that randomly varying increments within the desired range average out to an almost perfect sine wave with a frequency half way between the limits of the range (in the above example, about 11 Hz.). That is, the human body will tend to identify the signal as an 11 Hz sine wave rather than an unpredictable signal within the desired frequency range because the randomness is averaged out. In addition the signal feels repetitive and uninteresting. The term "body" is used below to describe any body, though typically a human body, which vibrates, and in or around which a change in the vibrational pattern is desired.

To overcome this limitation, a series of modifications are added to the program. First, to produce the desired signal with the desired frequency band and feel, the phase angle increments fed into the accumulator is programmed to jump randomly between three selections:

the first 20% of the desired range, (8.5 to 9 Hz)

the full desired range, (8.5 to 13.8 Hz) and the last 20% of the desired range, (13 to 13.8 Hz)

This jumping from mode to mode creates a signal that maintains frequency ranges for about ½ wavelength, which is long enough for vibrational patterns in the body to be strongly entrained by the signal for high effectiveness, and creates a feel of variability which is interesting to the therapy recipient. It also creates strong edges to the band width, providing strong power density between 8.5 and 9 Hz and minimal power density below 8.5 Hz.

Second, each random frequency within that signal is maintained for a randomly determined interval of about 1/20 wavelength, rather than following the sampling rate. This creates a low level randomness that gives the signal more of a chance to entrain the vibrational patterns in the body.

Third, Upward chirps are a therapeutic method that was discovered during the development of this signal generating method which is easily implemented through this method. An upward chirp, a brief signal of rising frequency, will tend to disrupt repeating vibrational patterns by entraining them and raising their frequency. A chirp that occurs at an unpredictable time, is of an unpredictable duration, and varies at an unpredictable rate of frequency change, can be highly effective at engaging and disrupting stagnant vibrational patterns in the body. Chirps can be ascending or descending, though ascending chirps are employed in the preferred embodiment. Including rising chirps within the signal, starting below a desired band, and ending in the band, will tend to entrain lower frequency rhythms within the body and lift them into the desired range, and also create an upward movement of rhythms within the desired range. Another series of chirps extending from the desired range to frequencies above that range will cause rhythms that used to be stuck within the frequency range to be lifted above that range.

By adding rising chirps, we make the signal far more effective at pulling stagnant vibrational patterns upward in frequency out of undesired ranges without supporting rhythms in the undesired ranges. Specifically, the range between 4 and 8 Hz has been found to be associated with physical pain and the range between 13 and 17 Hz, with worry. Stagnant EEG activity in the Alpha range 8-13 Hz is sometimes associated with attention deficit disorder and other behavior abnormalities. As the frequency of vibration in these tissues is raised pain is reduced, chronic inflammation and edema frequently vanish, or are attenuated to a significant extent, and worry decreases. Thus, while the random signal in the desired range is effective, the rising chirp through the undesired range into the desired range is significantly more effective. While the preferred embodiment increases frequency of these rising chirps linearly, it is certainly possible and probably desirable to have this frequency increase non-linearly to make it more unpredictable. Many of my pet theories of efficacy and mechanism are provided in this specification to provide deeper understanding to the reader. The claims should stand on their own merit and not be limited by such hypothetical theories.

Rising chirps can be inserted in a variety of ways. The preferred embodiment has one signal stopping and the rising chirp being inserted starting at the same phase angle as the end of the signal that stopped, to provide a signal with no discontinuity in amplitude, avoiding insertion of high frequency activity. Rising chirps can also be added by adding one signal to another with such things as an audio mixer or adding the values of both signals at each point in time. Rising chirps can also be added by inserting segments of a signal containing rising chirps into another signal. It is also possible to insert nothing but rising chirps, to produce a signal consisting of only rising chirps and frequency discontinuities between them. Chirps might also be employed without a desired range, but rather targeting an undesired range, sweeping upward or downward through the range to entrain vibrational patterns and pull them out of that range.

Fourth, segments of different signals are sequenced, or applied one after another in time such that amplitude and phase angle are continuous. This is an unexpected improvement in the therapeutic signal brought about as a result of the discovery that a signal with rising chirps is highly effective at engaging the vibrational nature of the body, frequently creating more pain in the process of inducing accelerated recovery or relieving pain. Sequencing different signals appears to release the pressure that causes additional pain while at the same time accelerating the release of the undesired vibrational pattern in the body. Normally a signal is applied to a body, creating stress as the vibrational activity builds up. This stress can build up and holds the vibration in a fixed way, causing additional pain, and potentially cellular damage. By shifting to another signal, which can be a signal of different amplitude, frequency, or other characteristics, a gentle transition between signals, or a signal of zero amplitude, the artificially induced stress in the body dissolves and another pattern of stress forms. Shifting from one form of stress to another allows the build-up of vibrational energy to change in unexpected ways, accelerating healing changes of vibrational patterns in the body. In the current embodiment, for frequencies in the range of 10 Hz, a randomly (unpredictably) varying signal duration of about 1 to 5 seconds (about 30 times the wavelength) is applied.

An example of sequencing would be applying a resonant frequency tone to a wine glass: The wine glass starts to resonate more and more, building up potential (vibrational) energy. By changing from this signal to other signals, we cause the built-up energy to take other forms within the wine glass. If, on the other hand, we continue the one resonant frequency for too long, the wine glass shatters. By this analogy we create more comfortable and natural changes in the body by providing a changing sequence of signals, rather than a single, continuous signal. By randomly varying the duration of each signal, we add a degree of unpredictability to the signal, encouraging the vibrational patterns of the body to reform in unpredictable, and more natural, ways.

These factors: inserting a string of phase angles into a sine function; producing an irregular signal by jumping from frequency to frequency and sub band to sub band; inserting rising chirps; and sequencing between different signals, provide a highly unpredictable non-linearly varying therapeutic signal that interacts well with the body and is highly efficacious. These methods were developed sequentially through the research that led to this invention, and are not at all obvious to someone who is familiar with the prior art. Sine waves of fixed frequency and linear sweeps in frequency of a sine wave are linearly varying signals that are well represented within the prior art of therapeutic signals.

Conclusions, Ramifications, and Scope

The preferred embodiment, as presented in FIGS. 1 and 2, while presenting a robust and flexible device for producing non-linear therapeutic signals, does not present the full extent of the potential applications of the claims. Any sort of signal can be inserted into phase angle accumulator (7) and any signal can be inserted at random intervals or for random periods of time. Random signals can be inserted into non-random signals such as tones or music. Also random signals can be inserted into existing signals in the EXCEL spreadsheet phase (12) by, for instance, adding a music signal and a random chirp signal, multiplying a signal with a random pause signal. Also, the specific methods employed in the preferred embodiment, such as LABVIEW and EXCEL, can be replaced with digital computer code, or the methods for producing random phase angle increments such as the 8-13 Hz signals or the upward chirps, can be replaced with other sorts of phase angle incrementation or oscillating signal synthesis. Also, the sine wave function might be replaced with any other sort of signal function that can be incremented. The method might be implemented in another form such that incrementation is replaced with another method of changing frequency such as delivering a variable voltage into an accumulator or integrator in an analog signal generator.

While the preferred embodiment includes only low frequency signals in the range of 2 to 13.8 Hz, any frequencies can be chosen and many frequency bands will be therapeutic. The audible ranges between 60 and 250 Hz and 250-2000 Hz are valuable as are ranges clear up to the megahertz range and probably beyond. Frequency ranges below 2 Hz are possible applications also. In each of these ranges, non-linear therapeutic signals will frequently be more therapeutic than signals with fixed or linearly varying frequency. The method of this invention can be used to imbed unpredictable signals into signals of any frequency.

While the preferred embodiment involves an analog amplifier and a mechanical transducer, non-linear therapy signals produced by this method can be delivered in a wide variety of ways like lasers, LED arrays, electrical pulse generators, electrical muscle stimulators, electrostatic plates, magnetic field generators, ultrasonic devices, pulsating lights or display screens, and acoustical speakers, and any other ways of producing a signal.

While the preferred embodiment is intended for humans and animals, this method might be applied to virtually any non-linear system, for instance, weather modification or smog processing, chemical processing, waste processing, liquid crystal structuring, etc, wherever injection of unpredictable signals might cause repeating vibrational patterns to dissipate or reform. Further objects and advantages of my invention will become apparent from a consideration of the drawings and ensuing description. Accordingly, the scope of the invention should be determined not by the embodiments illustrated, but by the appended claims and their legal equivalents.

Patent claims:

1. A method for creating a generally continuous therapeutic signal of non-linearly varying frequency comprising:

a. providing an increment generating means;

b. providing accumulation means for creating a string of accumulated totals using the sum of said increments; and c. providing a calculation means for calculating a therapeutic signal based on said string of accumulated totals;

d. providing a means for producing a therapeutic signal based on said string of accumulated totals;

wherein said increment generating means generates a non-linearly varying string of increments, said accumulation means creates a string of accumulated totals using sums of said increments, and said calculating means calculates a therapeutic signal based on said string of accumulated totals, and said means for producing a therapeutic signal produces a therapeutic signal based on said calculated string of accumulated totals.

2. The method of claim 1 wherein said calculation means is selected from sine and cosine functions.

3. The method of claim 1 wherein said increments have values that vary non-linearly.

4. The method of claim 1 wherein said non-linearly varying frequency falls within prescribed frequency limits.

5. The method of claim 4 wherein the value of said increments is updated between one and 50 times per cycle of said therapeutic signal.

6. A method for creating a generally continuous therapeutic signal comprising:

a) a first step for producing a variety of generally continuous signals; and b) a second step for selecting between said signals, whereby said second step selects among said signals, producing a resulting signal, that introduces no discontinuities in the amplitude of said resulting signal, and, whereby a non-linearly varying therapeutic signal is produced.

7. The method of claim 6 wherein said therapeutic signal comprises one or more of said signals falling within the lower part of said frequency spectrum, and one or more signals falling within the upper part of said frequency range.

8. The method of claim 6 wherein said second step selects a multiplicity of signals from each of the following groups; the first approximately 20% or less of said preselected frequency range, said preselected frequency range, and the last approximately 20% or less of said preselected frequency range.

9. A method for inserting a chirp into a therapeutic signal comprising:

a. creating a first therapeutic signal comprising a chirp with a first frequency band width, b. creating a second therapeutic signal with a second frequency band width c. switching between said first and said second signal, Wherein said first frequency band width comprises a portion of the said second frequency bandwidth, Whereby said switching between said first signal and said second signal produces a third therapeutic signal with chirp inserted.

10. The method of claim 9 wherein the starting frequency of said chirp is below said second frequency bandwidth and the ending frequency of said chirp is above lowest frequency of said second frequency bandwidth.

11. A method for increasing the frequency of rhythms in a living body comprising:

a. Selecting a desired range of frequencies, b. creating a plurality of upward chirps each comprising a part of said desired range, c. creating a therapeutic signal comprising a plurality of said upward chirps, applying said therapeutic signal to said living body for increasing said frequency of rhythm of said living body.

* * * * *